United States Patent [19]

Georgiades et al.

[11] Patent Number: 4,723,000
[45] Date of Patent: Feb. 2, 1988

[54] HUMAN INTERFERON GAMMA AND INTERLEUKIN-2

[75] Inventors: Jerzy A. Georgiades; Jerzy Gumulka, both of Houston, Tex.

[73] Assignee: BioSpectrum, Inc., Stafford, Tex.

[21] Appl. No.: 510,822

[22] Filed: Jul. 5, 1983

[51] Int. Cl.$^4$ .............................................. C07K 3/20
[52] U.S. Cl. .................................... 530/416; 530/351; 530/412; 530/417; 424/85; 435/68; 435/811
[58] Field of Search ....................... 260/112 R, 112 B; 424/85; 435/68, 811

[56] References Cited

U.S. PATENT DOCUMENTS

| | | | |
|---|---|---|---|
| 4,252,791 | 2/1981 | Grossberg et al. | |
| 4,257,938 | 3/1981 | Hosoi et al. | 435/811 |
| 4,285,929 | 8/1981 | Sugimoto et al. | |
| 4,289,690 | 9/1981 | Pestka et al. | |
| 4,296,025 | 10/1981 | Sugimoto | |
| 4,314,935 | 2/1982 | Uemura et al. | |
| 4,343,736 | 8/1982 | Uemure et al. | |
| 4,359,389 | 11/1982 | Heine | 424/85 |
| 4,376,822 | 5/1983 | Braude | |
| 4,382,027 | 5/1983 | Braude | |
| 4,390,623 | 6/1983 | Frabricius et al. | |
| 4,411,992 | 10/1983 | Gillis | |
| 4,411,993 | 10/1983 | Gillis | |
| 4,440,675 | 4/1984 | Brande | 424/85 |
| 4,490,289 | 12/1984 | Stern | 530/351 |
| 4,508,833 | 4/1985 | Sonnebern et al. | 530/351 |
| 4,541,952 | 9/1985 | Hosoi et al. | 530/351 |
| 4,551,271 | 11/1985 | Hochuli | 530/351 |

FOREIGN PATENT DOCUMENTS

| | | |
|---|---|---|
| 064401 | 2/1984 | European Pat. Off. |
| 56020519 | 6/1979 | Japan |
| 0068692 | 6/1981 | Japan ..................... 435/68 |
| 2061285A | 5/1981 | United Kingdom |

OTHER PUBLICATIONS

Mochizuki et al, *J. Immunol. Methods*, 39, 1980, pp. 185-201.
Gerard et al, *J. Immunol. Methods* (55), 1982, pp. 243-251, Chromatofocusing as a Tool for the ... Human IL-2.
Stadler et al, *Lymphokines* (6) 1982, pp. 117-135, Human IL-2.
Mier et al., *Lymphokines* (6), 1982, pp. 137-163, Human T Cell Growth.
*Lymphokine Res* 1(1), 1982, Summary of 3rd Internat. Symposium on Human Lymphokines.
Purification of IL-2 by Adsorption onto Perous Glass Beads. then Desorption, Abstract (Aginomoto KK).
The Complete Purification of Human Leucocyte Interferon, Berg et al, *Scand. J. Immunol* 71, 1980, pp. 489-502.
Georgiades, J. A., "Production and Purification of Human Interferon Gamma (HuIFN-γ)", Texas Reports on Biology and Medicine 41, 179 (1982).
Welte, K., et al., "Purification of Human Interleukin-2 to Apparent Homogeneity and Its Molecular Heterogeneity", *J. Exp. Med.*, 156, 454 (1982).
Frank, M. B. et al., "Biochemical and Biologic Characterization of Lymphocyte Regulatory Molecules, VIII, Purification of Interleukin-2 from Human T Cell Leukemia", *J. Immunol.*, 127, 2361 (1981).
Henderson et al., *J.Immunol.*, 131, 810 (1983).
Feldman et al., *Blood* 61, 815 (1983).
Friedman, *Arch. Pathol. Lab.* 106, 259 (1982).
Stadler et al., *J.Immunol.*, 128, 1620 (1982).
Yip et al., *Proc. Natl. Acad. Sci.* 79, 1820 (1982).
Harned et al., *J. Interferon Res.*, 2, 5 (1982).
Rubinstein et al., *Arch. Biochem. Biophys.*, 210, 307 (1981).
Gillis et al., *J.Immunol.*, 126, 1978 (1981).
Yip et al., *Proc. Natl. Acad. Sci.*, 78, 1601 (1981).
Lachman et al., *Lymphokines and Thymic Hormones: Their Potential Utilization in Cancer Therapeutics*, Raven Press, New York, 21 (1981).
Farrar, et al., *Lymphokines and Thymic Horomones: Their Potential Utilization in Cancer Therapeutics*, Raven Press, New York, 49 (1981).
Damme, et al., *Eur. J. Immuno.* 11, 937 (1981).
Georgiades et al., *Methods in Enzymology*, 78, 536, (1981).
Johnson et al, *Methods in Enzymology*, 78, 158 (1981).
Ferreira et al, *Arch. Virol.* 68, 27 (1981).
Heine et al., *J.Gen.Virol.*, 54, 47 (1981).
Northoff et al., *J. Immunol.*, 125, 1823 (1980).
Mier et al., *Proc. Natl. Acad. Sci.* 77, 6134 (1980).
Berg et al., *Scand. J. Immunol.*, 11, 489 (1980).
Pickering et al., *Ann. N.Y. Acad. Sci.*, 80, 354 (1980).
Aarden et al., *J. Immunol.*, 123, 2928 (1978).
Grob et al., *Biochemistry* 18, 5782 (1979).
Langford, et al., *Infection and Immunity* 26, 36 (1979).
Chadha et al., *J. Gen. Virol.* 43, 701 (1979).
Rubinstein, et al., *Proc. Natl. Acad. Sci.* 76, 640 (1979).
Braude et al., *J. Chromatography* 172, 207 (1979).
Georgiades et al., *Proc. Soc. Exp. Bio. Med.* 161, 167 (1970).
Edy et al., *J. Biological Chem.* 252, 5934 (1977).
Hajnicka et al., *Acta virol.* 20, 326 (1976).
Torma et al., *J. Biological Chem.*, 251, 4810 (1976).

(List continued on next page.)

*Primary Examiner*—John Kight
*Assistant Examiner*—Garnette D. Draper
*Attorney, Agent, or Firm*—Arnold, White & Durkee

[57] ABSTRACT

A process for producing unique human interferon gamma and interleukin-2 by chromatographic fractionation utilizing ion exchange and metal chelate chromatography. The interferon gamma and interleukin-2 are purified from crude interferon obtained by mitogen induction of human white blood cells.

9 Claims, No Drawings

OTHER PUBLICATIONS

Pokidova et al., *Antibiotiki* 10, 713 (1965).
Johnson et al., *The Journal of Immunology* 129:6, 2357-2359 (1982).
Weening et al., *Biochemical and Biophysical Research Communications* 104:1, 6-13 (1982).
Wiranowska-Steward et al., *Molecular Immunology* 17, 625-633 (1980).
Blalock et al., *Cellular Immunology* 49, 390-394 (1980).
Baron et al., *Annals New York Academy of Science*, 130-144 (1980).
Dianzani et al., *Infection and Immunity* 29:2, 561-563 (1980).
Goldstein, et al., *Microbiology, Parasitology and Infectious Diseases* 7, 560 (1979).
Langford et al., *The Journal of Immunology* 126:4, 1620-1623.

HUMAN INTERFERON GAMMA AND INTERLEUKIN-2

BACKGROUND OF THE INVENTION

This invention relates to the isolation and purification of various fractions including, among others, human interferon gamma (HuIFN-γ) and human interleukin-2 (IL-2) from heterogeneous crude interferon obtained by mitogen induction of human white blood cells.

THE PRIOR ART

Isolation and purification of either human interferon gamma or IL-2 from crude interferon is discussed in the prior art. See, e.g., U.S. Pat. No. 4,382,027 including the references cited in Col. 1, 11. 26–59; Georgiades, J. A., "Production and Purification of Human Interferon Gamma (HuIFN-γ)," Texas Reports on Biology and Medicine, 41: 179 (1982); Welt, K., Wang, C. I., Mertelsmann, R., Jenuta, S., Feldman, S. P., and Moore, M. A. S., "Purification of human interleukin-2 to apparent homogeneity and its molecular heterogeneity", *J. Exp. Med.*, 156:454 (1982) and Frank, M. B., Watson, J., Mochizuki, D., and Gillis, S., "Biochemical and biologic characterization of lymphocyte regulatory molecules. VIII. Purification of interleukin-2 from a human T cell leukemia", *J. Immunol.*, 127: 2361 (1981).

SUMMARY OF THE INVENTION

The processes of this invention are simple, effective and fast; can be conducted as either a batch or a continuous operation; are consistently repeatable and are applicable to large quantities of crude interferon. Mild conditions substantially preclude protein denaturation or alteration. Bacterial and fungal contamination are avoided.

The invention is most effectively practiced utilizing sequential cation exchange and metal chelate chromatographic fractionation of crude interferon. No buffer exchanges are required between the chromatographic columns which can therefore be automatically operated in tandem to produce highly purified human interferon gamma. Only one buffer exchange is required for the production of purified human IL-2.

DETAILED DESCRIPTION OF THE INVENTION

Heterogeneous crude interferon useful in the practice of this invention may be obtained in a conventional manner from human peripheral blood leukocytes. See, e.g., U.S. Pat. Nos. 4,376,821 and 4,376,822 and references cited.

In the preferred practice of the invention, buffy coats containing about 70% to 90% lymphocytes and about 10% to 30% leukocytes are centrifuged to remove plasma, the sedimented cells washed with saline, and the wash liquor removed by centrifugation. The cells are then suspended, preferably in a concentration of from about $1 \times 10^5$ to about $1 \times 10^7$ cells/ml. in a first stage induction medium comprising RPMI or equivalent culture, supplemented with (i) about 0.5% to about 1.5% by volume of a gamma serum and about 2.5% to about 7.5% by volume of human albumin to provide a protein content of from about 1 to about 1½ mg/ml. and (ii) about 8 to about 12 micrograms (ug)/ml. of gentamycin and (iii) about 0.5 to about 1.5 millimoles (mM) hepes-tricine. From about 75 to 125 nanograms (ng/ml. of staphylococeal enterotoxin B (SEB) is added, and the culture maintained at approximately 37° for a time period of from about 90 to about 100 hours. The cells are then harvested, washed with unsupplemented RPMI 1640, separated by centrifuge and resuspended in a second stage induction medium similar to the first stage, with the exception that SEB is replaced with from about 175 to about 225 ug/ml. of phytohemagglutinin (PHA), and the culture maintained at approximately 37° for a time period of from about 40 to about 50 hours. The liquid phase is heterogeneous crude interferon which is processed in accordance with this invention to yield various protein fractions including human interferon gamma and interleukin-2.

PURIFICATION PROCEDURES

Step 1—Heterogeneous crude interferon is appropriately clarified and concentrated prior to purification. In a preferred embodiment of the invention, crude interferon is concentrated to about one third to one fifth its original volume by use, in tandem, of at least two membrane cassette systems of the type produced by Millipore Corporation, Bedford, Mass. For example, crude interferon containing from about 0.5 to about 1.5 mM/liter of ethylenediamine tetraacetic acid (EDTA) tetrasodium salt is clarified by passage through a Millipore cassette provided with a five square foot membrane having a pore size of 0.5 microns. The clairified ultrafiltrate is introduced into a second Millipore cassette provided with a five square foot membrane of a pore size to preclude passage of material having a molecular weight in excess of about 10,000. The procedure is continued until approximately an 80% reduction in the original crude interferon volume is achieved. The concentrate consisting of material of molecular weight greater than 10,000 is collected and desalinated. A preferred desalination procedue entails combining the concentrate with approximately an equal volume of deionized water, passing the resulting mixture through a Millipore cassette provided with a 10,000 molecular weight cut-off membrane to permit separation of water from the concentrate, diluting the concentrate again with approximately an equal volume of deionized water and again passing it through the cassette, this procedure being repeated until the concentrate is virtually salt-free, as evidenced by the fact that its electrical conductivity is about zero.

Step 2—Cation Exchange Chromatography: Heterogeneous crude interferon, preferably concentrated and desalinated as described in Step 1, is adjusted to a pH of from about 6 to about 7.5 with an appropriate acid such as 50% acetic acid and quickly cooled to a temperature in the range of from about 4° to about 15° C., preferably about 12° C.

To practice this step as a batch operation, the cooled desalinated concentrate is first mixed with a relatively weak cation exchange matrix, e.g., cross-linked dextran, a water insoluble poysaccharide including a cross-linked agarose gel or a carboxymethyl cellulose such as CM-Sepharose CL-6B beads (Pharmacia Fine Chemicals) or equivalent, previously activated, for example, with 0.02M sodium acetate (pH 6.0–6.3) at a temperature from about 0° to about 10° C., preferably about 4° C., for about 30 to about 120 minutes, preferably for approximately one hour. The ratio of the volume of ion exchange beads to the original volume of concentrate is appropriately within the range of from about 1:25 to about 1:55, preferably from about 1:35 to about 1:45. From about 85% to about 95% of the interferon gamma and IL-2 proteins present in the crude interferon binds to the beads.

The ion exchange beads having the interferon gamma and IL-2 proteins bound thereto are transferred onto a chromatographic column. Excess liquid is removed from the column under reduced pressure. The beads are first washed with 0.01M to 0.05M, preferably about 0.02M sodium acetate with a pH of from about 5.5 to about 6.5, preferably from about 6.0 to about 6.3, until optical density at 280 nm is about 0. The beads are then washed with buffered sodium phosphate solution, preferably 0.02M, sodium phosphate, pH 7.

The adsorbed human interferon gamma and IL-2 proteins are eluted with a phosphate buffer, such as phosphate buffered saline (PBS),[1] at a pH of from about 7 to about 8, preferably from about 7.2 to about 7.4, at a temperature of from about 0° C. to 20° C., preferably about 4° C. Two to five hundred fold purification of human interferon gamma and substantial purification of IL-2 is achieved at this stage.

[1] PBS is a standard biological solvent composed of 0.9% NaCl in water, adjusted to a pH 7.2 with phosphate buffer.

When the process of the invention is practiced as a continuous operation, the cooled desalinated concentrate is added directly to a cation exchange matrix previously loaded into an appropriate column.

Step 3—Metal Chelate Chromatography: The Step 2 eluate is applied directly to a chromatographic column having a chelating matrix. The metal chelate carriers used in the invention may be polysaccharides or cross-linked polyolefins which have chelating groups such as a bis carboxymethyl amino group to which a metal ion is bound. Commercially available products of this type include Sepharose 6B beads (Pharmacia Fine Chemicals), tetraethylenediamine agarose (Pierce), or equivalent. In the preferred practice of the invention, a Sepharose 6B matrix is previously charged with ions, such a zinc ion, to which the interferon gamma and IL-2 proteins do not bind. The column is washed with PBS+1M NaCl[2] at pH 7.2 to 7.4, and operated at a temperature of about 2° C. to about 20° C., preferably about 4° C. The not adsorbed material contains a major proportion, for example, on the order of 90% to 100%, of the interferon gamma and IL-2 activity present in the crude interferon starting material.

| [2] PBS + 1M NaCl buffer is prepared as follows: |
| --- |
| (a) Stock solution A (1 liter) |
| 80 gms NaCl |
| 2 gms KCl |
| 1 gm CaCl$_2$ |
| 1 gm MgCl$_2$—6H$_2$O |
| Injectable water to provide 1 liter of solution |
| (b) Stock solution B (1 liter) |
| 21.7 gms Na$_2$HPO$_4$—7H$_2$O |
| 2 gms KH$_2$PO$_4$ |
| Injectable water to provide 1 liter of solution, mix well. |
| (c) PBS + 1M NaCl Buffer |
| 100 ml Stock solution A |
| 300 ml Injectable Water |
| 100 ml Stock solution B |

| [2] PBS + 1M NaCl buffer is prepared as follows: |
| --- |
| 58.5 gm NaCl |

[1] Mix the ingredients in the order listed.
[2] Injectable water to provide 1 liter of solution
[3] pH = 7.3 + 0.1

Alternatively, the chelate matrix, such as Sepharose 6B beads, may be charged with metal ions such as cupric ions to which the interferon gamma and IL-2 proteins do bind. When such a column is used, elution is accomplished in a manner known to the art.

Step 4—Removal of SEB(optional): An immunological column may be used to remove residual quantities of the SEB utilized in the induction and which remain, e.g., in the eluate from Step 3 or in other fractions separated from the crude interferon starting material. The column matrix appropriately consists of a water insoluble polymeric material having an SEB antibody bound, preferably convalently, thereto by procedures well known to the art such as the CNBr process described, e.g., in Axen, et al., Nature (London) 214:1302 (1967) or the processes described in U.S. Pat. No. 3,720,760. CNBr-Sepharose-4B (Pharmacia Fine Chemicals) having an SEB antibody covalently bound to the surface is preferred.

The not adsorbed material from Step 3 is added directly to the immunological column. Careful control of the flow rate results in the removal of more than 90% of any SEB present.

Step 5—Affinity Chromatography: The non-adsorbed material from Step 3 or from Step 4 is directly applied at a temperature within the range of 0° C. to 20° C., preferably about 4° C., on a Concanavalin A (Con A)-Agarose (product of Bethesda Research Laboratories, Bethesda, Md.) or equivalent matrix, e.g., lentil lectin Sepharose or pea lectin Sepharose in a column. The column is washed with PBS, preferably at least twice, and eluted with PBS containing 0.1M methyl-alpha-D-mannopyranoside or from 0.1 to 2.0M alpha-methyl-D-mannoside or 1-methyl-D-glucoside at a pH of approximately 7.1.

Replacement of the Con A matrix with phenylboronate agarose (Amicon) beads provides an attractive alternative. The substantial entirety of the interferon gamma binds to the phenylboronate agarose matrix. Elution may be accomplished with dilute solutions of sorbitol containing small amounts of sodium chloride. The washing sequence appropriately entails PBS, 0.1M sorbitol+1.0M NaCl, and 0.5M sorbitol+1.0M NaCl, followed by a final PBS wash.

Utilization of the phenylboronate agarose matrix eliminates the possibility of contamination of the purified interferon gamma product by leakage of Con A from the chromatographic matrix.

The eluate is the purified human interferon gamma product of this invention. At least 7700 fold purification of human interferon gamma is achieved by this procedure.

The purified human interferon gamma product has a specific activity of at least $1 \times 10^7$ units (u)/mg. protein. It is stable at +4° C. for at least 12 weeks; free of inducer, IL-1, IL-2 and IL-3. It has an undetectable level of lymphotoxins, MIF, chemotactic factors. Undetectable levels of other types of interferons are evidenced by absence of the interferon activity of Bovine Embryo Kidney Cells (BEKC) and by sensitivity to heating and pH 2. The product is not neutralized by specific anti-human interferon alpha, beta or by a mixture of anti-alpha/anti-beta antibodies. It is neutralized by specific antibodies against interferon gamma. It can be lyophilized directly without loss of activity.

Step 6

IL-2 Purification:

The not adsorbed fraction from Step 5 is processed to exchange the phosphate-sodium chloride buffer with tris(hydroxymethyl)amino methane (tris) or equivalent, and the pH is adjusted to from about 9.0 to about 9.8.

The prepared fraction is applied to relatively strong anion exchange matrix in a chromatographic column. Appropriate matrices comprise water insoluble polysaccharide or cellulosic carries associated with anion exchange agents such as quarternary ethyl amines, diethylaminoethylene and the like. The preferred matrices are quarternary ethylamine (QAE)-Sephadex A-50 and diethylamino ethylene (DEAE)-Sephadex A-50 (Pharmacia Fine Chemicals).

The column is washed with a sequence of buffers, preferably of the same composition as the buffer present in the prepared fraction, but of progressively decreasing pH, e.g., 8.0; 7.5; 7.0 and 6.5, ending with a buffer of pH 6.5 containing 1.0M sodium chloride.

Fractions eluted from the range of buffers with pH 7.0 to 6.5 are assayed for IL-2 activity which is expressed in Growth Supporting Units (GSU). The fractions showing IL-2 are pooled.

The purified IL-2 product of the invention yields a single isoelectric focusing band at a pH value of about 6.8 to 6.9; contains at least 3500 GSU/mg. protein and is stable for 60 days at 4° C. in the presence of polyethyleneglycol of about 6000 molecular weight.

EXAMPLE I

Preparation of Crude Interferon

Buffy coats containing about 80% lymphocytes and about 20% leukocytes are pooled and centrifuged at about 2000 RPM to remove plasma. The sedimented cells are washed with saline and centrifuged to remove the wash liquor. The washed cells are suspended at a concentration of about $4 \times 10^6$ cells/ml. in a RPMI 1640 culture medium contained in roller bottles and supplemented with 1% by volume of agamma serum and 0.5% by volume of human albumin to provide a protein content of about 1.2 mg/ml. and with 100 ng/ml. staphylococeal enterotoxin B (SEB). The RPMI also contains approximately 10 ug/ml. of gentamycin and one mM of hepes-tricine. The roller bottles are incubated at 37° for 96 hours. The cells are then harvested and washed with unsupplemented RPMI 1640, separated from the RPMI by centrifuge, and resuspended in a second stage induction medium contained in roller bottles. The second stage medium is like the first stage except that SEB is replaced by 200 ug/ml. of phytohemagglutinin (PHA). The bottles are maintained at approximately 37° for approximately 48 hours. The "crude interferon" liquid phase of the culture is separated by certrifuge.

EXAMPLE II

Clarification and Concentration 77 liters of crude interferon produced in the manner described in Example I containing approximately about 1 millimole/liter of ethylenediamine tetraacetic acid (EDTA) sodium salt was clarified by passage through a Millipore cassette provided with a 5 square foot membrane having a pore size of 0.5 microns utilizing a Procon pump. The clarified ultrafiltrate was passed through a second Millipore cassette provided with a 5 square foot membrane of a pore size to preclude passage of material having a molecular weight in excess of 10,000. A final concentrate consisting of approximately 15 liters of material in excess of 10,000 molecular weight is collected and further processed in accordance with this invention to provide purified interferon gamma and IL-2.

Data characterizing the crude interferon and the concentrate are set forth in Table I.

TABLE I

| | ORIGINAL VOLUME (CRUDE INTERFERON) | FINAL VOLUME (CONCENTRATE) |
|---|---|---|
| Volume (Liters) | 77 | 15 |
| Protein Concentrate (mg/ml.) | 1.5 | 2.18 |
| Titer | | |
| SBV* | $10^{3.5}$ | $10^{4.2}$ |
| VSV** | $10^{2.5}$ | $10^{3.5}$ |
| Total Gamma Interferon Units | $243 \times 10^6$ | $243 \times 10^6$ |
| Specific Gamma Interferon Activity (SBV Titer) | $2.1 \times 10^3$ | $7.2 \times 10^3$ |

*Sindbis Virus
**Vesicular Stomatitis Virus

The concentrate is combined with approximately an equal volume of deionized water, and the resulting mixture is passed through a Millipore cassette provided with a 10,000 molecular weight cut-off membrane. The concentrate is recycled and again diluted with deionized water and passed through the cassette until it is substantially salt free as evidenced by the substantial absence of electrical conductivity.

EXAMPLE III

Purification of Interferon Gamma

Step 1—Cation Exchange Chromatography: The salt free concentrate was adjusted to pH 6.55 with 50% acetic acid and cooled to approximately 12° C. The cooled material was mixed for about one hour at 4° C. with 2000 milliliters of CM-Sepharose CL-6B ion exchange beads which had been equilibrated at pH 6 to 6.3 with 0.02 molar sodium acetate. The ion exchange beads with bound proteins were then put into a column and washed with 0.02 molar sodium acetate until the optical density of the effluent at 280 nm reached about 0. The column was then washed with 0.02 molar sodium phosphate buffer pH 7 until the optical density at 280 nm again approximated 0.

The column was then eluted with PBS + 1M NaCl. The specific interferon gamma activity of the eluate was $4.7 \times 10^5$. Purification at this stage was 223 fold and recovery was 128% calculated on the crude interferon.

Step 2—Metal Chelate Chromatography: The eluate from step 1 containing 627 mg. total protein was applied directly to a column containing chelating Sepharose 6B charged with zinc ions and equilibrated with PBS + 1M NaCl. The column was washed with the equilibration buffer to remove unbound proteins. The not adsorbed fraction contains 330 mg. total protein which includes IL-2 activity and substantially all the applied interferon gamma activity.

The specific activity of interferon gamma was $10^6$, representing two fold purification of the production of Step 1.

Step 3—Concanavalin A (Con A) Agarose Affinity Chromatography: The non-adsorbed material from Step 2 was directly applied to a Con A column at 4° C. About 14% of the total protein present in adsorbed material from Step 2 binds to the Con A matrix. The adsorbed material is eluted with 0.1M alpha-mannopyranoside in 1.0 M NaCl and 1.0 M alpha-mannopyranoside in 1.0M NaCl to provide the purified human interferon gamma of this invention.

by this process 666.6 fold total purification and 188% recovery of interferon gamma calculated on the crude interferon was achieved.

The purified interferon gamma product has a specific activity of about $1 \times 10^7$ u/mg. protein, is stable at $+4°$ C. for at least 12 weeks, is substantially free of interferon gamma inhibitors, IL-1, IL-2 and IL-3, and has an undetectable level, if any, of lymphotoxins and MIF (macrophage migration inhibition factor) and of alpha and beta interferon, is sensitive to pH 2 and loses activity in about 1 to 2 hours at 56° C.

To remove the unbound protein which includes IL-2, the column was washed with PBS until the optical density at 280 nm reached 0. Approximately 1,000 ml. of non-adsorbed material was obtained.

EXAMPLE IV

Purification of IL-2

The 1,000 ml. unadsorbed fraction obtained in Step 3 was processed to exchange the PBS-sodium chloride buffer with 0.1M Tris-HCl pH 9 buffer. The buffer exchange was accomplished by adding an equal amount of the Tris-HCl pH 9 buffer to the 1,000 ml. unabsorbed fraction from Step 3 and thereafter passing the mixture through a Millipore cassette provided with a 1,000 molecular weight cut-off membrane, the concentrate being recycled and again diluted with an equal volume of Tris buffer, and the process repeated through approximately five such dilutions or until the pH of the concentrate was approximately 9. The prepared fraction was then applied on QAE-50 Sephadex column. The column was then washed with a series of Tris buffer washes beginning with 60 ml. of the starting buffer followed by similar buffers of decreasing pH (8.0; 7.5; 7.0; 6.5) and ending with 0.1M Tris buffer pH 6.5 containing 1.0M sodium chloride. Fractions eluted from the range of buffers with pH 7.0 to 6.5 were assayed for IL-2 activity which is expressed in Growth Supporting Units (GSU). The fractions showing IL-2 activity were pooled. Total volume of 100 ml. of pooled fractions contained 40,000 GSU and 10 mg. of protein (4,000 GSU/mg protein). Isoelectrofocusing of the obtained material showed only one distinguishable band with the pH value of 6.9–6.8. The IL-2 product can be directly lyophilized and reconstituted without significant loss of GSU.[3]

[3] One GSU is the amount of IL-2 required to support growth of $10^4$ T-lymphocytes for a period of 7 days.

What is claimed is:

1. In a process including chromatographic fraction steps for the purification of crude interferon produced by the mitogen induction of human white blood cells to provide interferon gamma or interleukin-2, the improvement of which comprises utilization of cation exchange chromatography as the first chromatographic fraction step, and thereafter the eluate from the cation exchange chromatography fractionation step is subjected directly to further fractionation by metal chelate chromatography charged with zinc ions or cupric ions.

2. The process for the production of human interferon gamma and interleukin-2 from crude interferon produced by the mitogen induction of human white blood cells which comprises:
   (i) first fractionating the crude interferon by cation exchange chromatography and eluting the proteins containing interferon gamma and interleukin-2 from the cation exchange matrix;
   (ii) subjecting the eluate from step (i) to fractionation by metal chelate chromatography charged with zinc ions or cupric ions;
   (iii) directly subjecting the fraction from step (ii) containing interferon gamma and interleukin-2 to fractionation by affinity chromatography utilizing a matrix to which only the interferon gamma binds and to which interleukin-2 does not bind and eluting the bound interferon gamma from the matrix; and
   (iv) recovering the eluate from step (iii) as a purified interferon gamma product.

3. A process as defined in claim 2 in which (v) the not adsorbed fraction from step (iii) is further fractionated by ion exchange chromatography utilizing an ion exchange matrix to which interleukin-2 binds and (vi) the bound interleukin-2 is thereafter eluted to provide a purified interleukin-2 product.

4. The process for the production of human interferon gramma and interleukin-2 from crude interferon produced by the mitogen induction of human white blood cells which comprises:
   (i) first fractionating the crude interferon by cation exchange chromatography and eluting the proteins containing interferon gamma and interleukin-2 from the cation exchange matrix;
   (ii) subjecting the eluate from step (i) to fractionation by metal chelate chromatography; charged with zinc ions or cupric ions
   (iii) directly subjecting the fractions from step (ii) containing interferon gamma and interleukin-2 to fractionation by affinity chromatography utilizing a matrix to which only the interferon gamma binds and to which interleukin-2 does not bind and eluting the bound interferon gamma from the matrix;
   (iv) further fractionating the non-absorbed fraction of step (iii) by ion exchange chromatography utilizing an ion exchange matrix to which interleukin-2 binds; and
   (v) eluting the bound interleukin-2 to provide purified interleukin-2.

5. The process of claim 2 or 4 in which the column matrix utilized in step (iii) is a Concanavalin A matrix.

6. The process of claim 2 or 4 in which the column matrix utilized in step (iii) is a phenylboronate matrix.

7. A process as defined in claim 2 or 4 in which the fraction from step (ii) that contains interferon gamma and interleukin-2 is passed through an immunological column to remove residual mitogen prior to fractionation by affinity chromatography in step (iii).

8. In a process, including chromatographic fractination steps, for the purification of human interleukin-2, produced from mitogen-induced human white blood cells, the improvement comprising utilization of metal chelate chromatography, said metal consisting essentially of cupric ions.

9. A process according to claim 8, comprising the additional improvement of cation exchange chromotagraphy as a step performed prior to said metal chelate chromatography.

* * * * *